United States Patent [19]

Strom

[11] Patent Number: 5,669,869

[45] Date of Patent: Sep. 23, 1997

[54] IMPOTENCE AID

[76] Inventor: Arnold J. Strom, 175-No. McKnight Rd., Apt. 308, St. Paul, Minn. 55119

[21] Appl. No.: 650,810

[22] Filed: May 20, 1996

[51] Int. Cl.⁶ .................................................... A61F 5/00
[52] U.S. Cl. ................................................ 600/38; 600/39
[58] Field of Search ................................... 128/842, 843, 128/844; 600/38–41

[56] References Cited

U.S. PATENT DOCUMENTS

| | | | |
|---|---|---|---|
| 4,224,933 | 9/1980 | Reiling | 600/39 |
| 4,989,592 | 2/1991 | Chang | 600/38 |
| 5,083,556 | 1/1992 | Osborn | 600/39 |
| 5,468,211 | 11/1995 | Welch | 600/38 |

Primary Examiner—Michael A. Brown
Attorney, Agent, or Firm—American Innovations Esq; Dorothy Morse

[57] ABSTRACT

A hand-held cylindrical device, and method for its use, comprising a flexible collar fitting over a flared flange on one of its open ends and a threaded cap on its other open end. A one-way valve is connected through the threaded cap so that as a penis is inserted into the cylinder, the collar forms a seal around the penis forcing air out of the cylinder through the one-way valve. After insertion, and when the cylinder is partially drawn away from the penis, the one-way valve closes and a vacuum is formed within the cylinder causing blood to be drawn into the penis, thereby enlarging it. Repeated massaging movement of the cylinder, by hand or through an electrical device creating reciprocal movement which is attached to the cap, or the use of a condom within the cylinder, causes more stimulation and additional enlargement until the penis is fully erect.

11 Claims, 2 Drawing Sheets

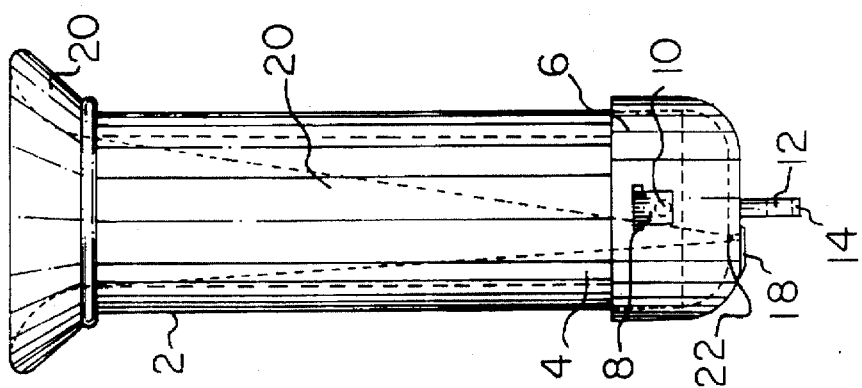
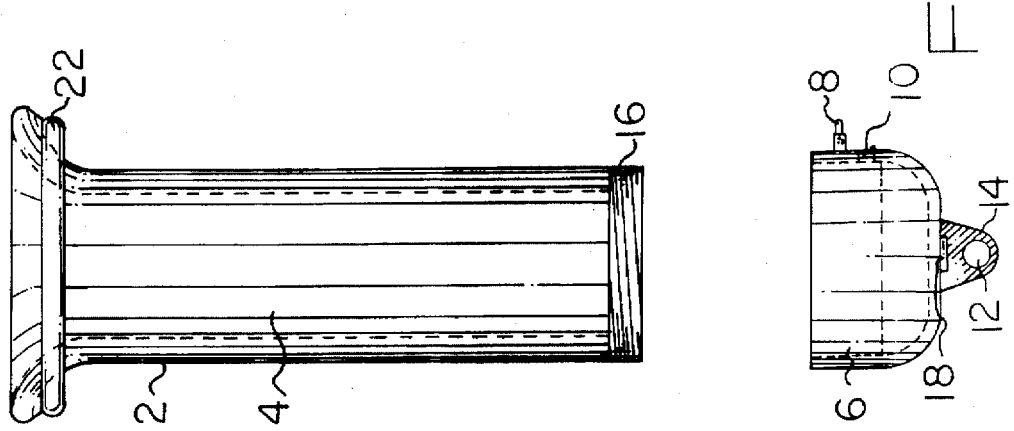
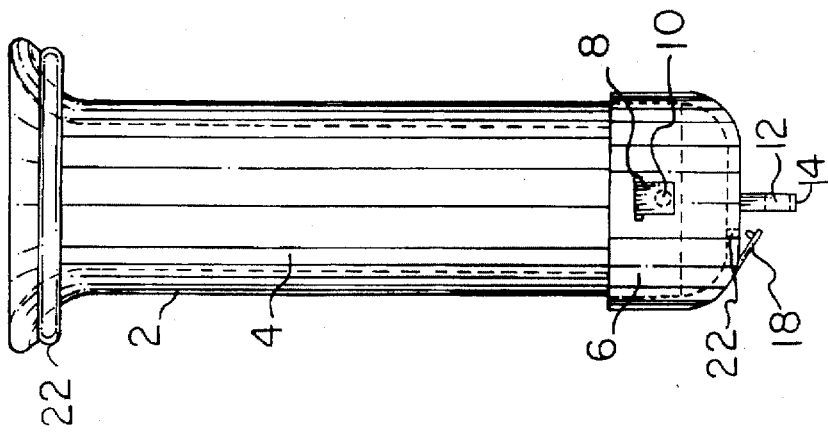

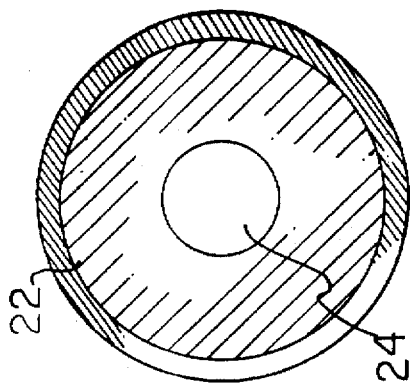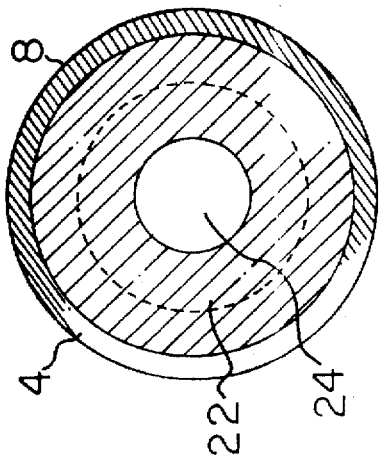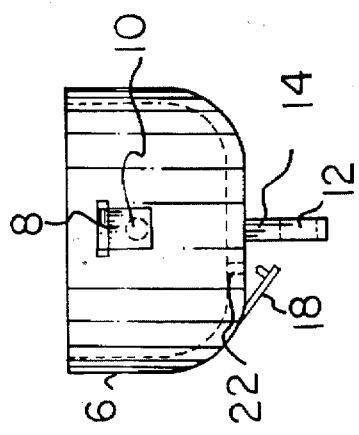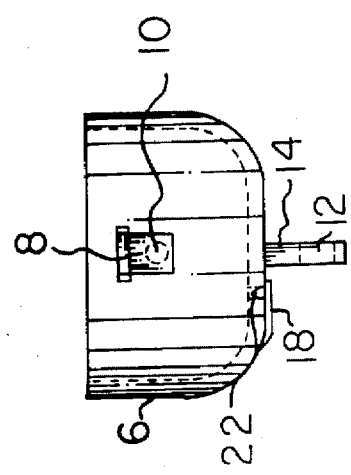

IMPOTENCE AID

BACKGROUND - FIELD OF INVENTION

This invention relates to methods and devices used in the treatment of impotency, specifically to a hand-held cylindrical device, and a method for its use, comprising a flexible collar fitting over a flared flange on one of its ends and a threaded cap on its other end through which a one-way valve is connected so that as a penis is inserted into the cylinder, the collar forms a seal around it, forcing air out of the cylinder through the one-way valve, and after insertion, when the cylinder is partially drawn away from the penis, the one-way valve closes and a vacuum is formed within the cylinder causing blood to be drawn into the penis, thereby enlarging it. Repeated movements of the cylinder, by hand or through an electrical device creating reciprocal movement which is attached to the cap, or the use of a condom within the cylinder, enhance stimulation of the penis and cause additional enlargement until the penis is fully erect.

BACKGROUND - DESCRIPTION OF PRIOR ART

Male impotence is not an uncommon problem and both surgical implants and non-invasive devices are known for its treatment. Surgical implant procedures are expensive and subject the patient to the common risks associated with all types of surgery. Known non-invasive procedures are less expensive, but are sometimes cumbersome and complicated to use. A number of non-invasive treatment devices comprise the use of a constriction band for placement around the base of a penis to help it maintain an erection by preventing the outflow of blood from the penis once it has obtained an erect state. Other non-invasive treatment devices comprise cylinder and a vacuum pump combinations for evacuating air from the cylinder to cause blood to flow into a penis inserted therein, and combinations involving a constriction device, a cylinder, and a vacuum pump.

An example of a constriction device is disclosed in the invention in U.S. Pat. No. 5,218,974 to Garrett (1993) which comprises a flexible strap for encircling a penis that is attached to a belt worn about the lower torso of a male. A constriction device, cylinder, vacuum pump combination impotence aid is disclosed in the invention in U.S. Pat. No. 5,115,800 to Matejevic (1992) which comprises an elastic ring attached to the open end of a tube into which a penis is placed. A bellows-type vacuum pump connected to the Matejevic tube reduces air pressure within the tube causing the penis to reach an erection. A lever connected to the Matejevic tube is then activated to release the elastic ring onto the base of the penis so as to maintain the erection. The elastic ring must be quickly disconnected immediately prior to ejaculation for semen to be normally expelled. Another constriction device, cylinder, and vacuum pump combination impotence aid is disclosed in U.S. Pat. No. 4,378,009 to Osbon, Sr. (1983) which comprises an elastic constriction device carried on the end of a cylinder that is connected by a flexible conduit to a vacuum source, and wherein the elastic constriction device is released just at the correct moment to capture an erection. A similar combination constriction device, cylinder, and vacuum pump impotence aid, disclosed in U.S. Pat. No. 5,125,890 to Merrill (1992), uses a vacuum release lever to simultaneously release the vacuum within the cylinder and dislodge a constriction band for immediate, automatic placement around the base of the penis inserted into the cylinder. The invention in U.S. Pat. No. 5,295,946 to Collins (1994) provides a slightly different constrictive invention, having an inflatable cuff for encircling the base of the penis and which extends distally to provide a tourniquet action for trapping blood within a penis to increase its rigidity. In contrast to the devices using constrictive bands around the base of the penis, the present invention is more comfortable to use and less likely to cause strangulation of the penis.

There are also many impotence aid inventions comprising cylinders and vacuum pumps. The inventions in U.S. Pat. No. 5,213,563 to Cox (1993) and U.S. Pat. No. 5,095,895 to Walsh (1992) disclose cylinders attached to manually operable pumps to evacuate air from the attached cylinder. The invention in U.S. Pat. No. 5,462,514 to Harris (1995) discloses a cylinder integrally mounted to an electrically powered vacuum generating unit. In contrast, the present invention has a basic principle of operation different from other known impotence aids in that the present invention functions similarly to a conventional piston and cylinder assembly wherein the piston moving forward within a conventional cylinder forces air out of the conventional cylinder through a one-way valve which thereafter closes when the piston is drawn back, thereby creating a vacuum. Also, the present invention is less cumbersome and less expensive to construct and use than known prior art.

SUMMARY OF INVENTION - OBJECTS AND ADVANTAGES

It is the primary object of this invention to provide an impotence aid which functions similarly to a conventional piston and cylinder assembly wherein the piston moving forward within a conventional cylinder forces air out of the conventional cylinder through a one-way valve which thereafter closes when the piston is drawn back, thereby creating a vacuum. A further object of this invention is to provide an impotence aid which will be simple to use and effective. It is also an object of this invention to provide an impotence aid which will less cumbersome to construct and use than prior art devices comprising the use of vacuum pumps. A further object of this invention is to provide an impotence aid which is less expensive to make and use than prior art devices comprising the use of vacuum pumps. It is also an object of this invention to provide an impotence aid which does not require the use of a constriction band for maintaining an erection. It is also and object of this invention to provide means for additional enlargement of a penis until the penis is fully erect through repeated movement of the cylinder, by hand or through an electrical device attached to the cap which creates reciprocal movement, or through the use of a condom secured within the cylinder.

As described herein, properly manufactured and used as an impotence aid, the present invention would provide a device for both creating and maintaining an erection. The present invention functions similarly to a conventional cylinder and piston assembly whereby the piston, or penis, moving forward within the cylinder forces air out of the cylinder through a one-way valve which thereafter closes when the piston, or penis, is drawn back, thereby creating a vacuum. The interior surface of the cylinder is very smooth and when the cylinder interior is lubricated, massaging movement of the cylinder about a penis inserted therein effects a delightful sensation which further stimulates and helps maintain a penile erection. A threaded cap attached to one end of the cylinder, a one-way valve positioned over an aperture in the cap, and a flexible collar having a centrally located opening therethrough for forming a seal around an inserted penis, the flexible collar being attached to the end of the cylinder remote from the cap, in combination aid the inserted penis in displacing air from the interior of the cylinder through the one-way valve in the cap. Subsequently, when the cylinder is partially drawn away from the penis, a vacuum is created causing blood to be drawn into the penis to enlarge it. Thereafter, repeated massaging movements of the cylinder to cause additional enlargement until the penis is fully erect, may be accomplished either by hand or by attachment of a device applying reciprocating movement to the cap, or additional enlargement of the penis may be accomplished through the use of a condom having lubricant therein which is secured within the cylinder. A slot through the cap of the present invention, and a snapping device attached to the cap adjacent to the slot, secure the closed end of a condom so that the open end of the condom may be stretched across the flanged end of the cylinder remote from the cap and secured by the collar. The present invention is simpler to use, less cumbersome, and less expensive to make and use than impotence aids connected to vacuum pumps. Also, the present invention does contemplate the need for constriction bands which may be uncomfortable and could strangulate a penis.

The description herein provides preferred embodiments of the present invention but should not be construed as limiting the scope of the impotence aid invention. Variations in the length of the cylinder, the material from which the cylinder and cap are made, the thickness of the walls of the cylinder, the configuration of the bracket attached to the cap, the type of one-way valve used to help create a vacuum within the cylinder during use, the configuration of the flanged end of the cylinder, the configuration of the slot and snapping device used to secure the closed end of a condom to the cap, the type of lubricant used, the material from which the collar is made, and the thickness of the collar, other than those shown and described herein, may be incorporated into the present invention. Thus the scope and intent of the present invention should be determined by the appended claims and their legal equivalents, rather than the examples given.

BRIEF DESCRIPTION OF THE DRAWINGS

FIG. 1 is a side view of the invention with a threaded cap attached to the cylinder.

FIG. 2 is a side view of the invention without the threaded cap attached.

FIG. 3 is a side view of the invention with a condom positioned within the cylinder.

FIG. 4 is a left side view of the threaded cap of the invention.

FIG. 5 is a side view of the threaded cap of the invention having a condom securing snap in an open position.

FIG. 6 is a side view of the threaded cap of the invention having a condom securing snap in a closed position.

FIG. 7 is a top view of the invention collar and its centrally positioned opening.

FIG. 8 is a top view of the invention collar positioned on cylinder 4.

DETAILED DESCRIPTION OF PREFERRED EMBODIMENTS

FIG. 1 shows a preferred embodiment of an impotence aid invention 2 having a cylinder 4 and an internally threaded cap 6 attached to one end of cylinder 4. It is contemplated for cylinder 4 to be sufficiently large to contain an erect penis (not shown). The other end of cylinder 4 is flared and open. The thickness of the walls of cylinder 4 is not critical to impotence aid invention 2. However, the interior surfaces of cylinder 4 must be very smooth so that when the interior surfaces of cylinder interior are lubricated, massaging movement of cylinder 4 about a penis (not shown) which is inserted therein imparts a delightful sensation which further stimulates the penis and helps maintain a penile erection. Although not shown, impotence aid invention 2 functions similarly to a conventional cylinder and piston assembly whereby the piston, or penis, moving forward within the cylinder forces air out of the cylinder through a one-way valve 8 which thereafter closes when the piston, or penis, is drawn back, thereby creating a vacuum.

FIG. 1 shows a collar 22 attached to the flared end of cylinder 4. It is contemplated for collar 22 to be made of a flexible material, such as a silicone rubber. FIG. 1 also shows cap 6 having an aperture 10 therethrough and one-way valve 8 positioned on cap 6 so as to close aperture 10 and allow air to only exit from cylinder 4. FIG. 1 further shows cap 6 having a slot 26 positioned on the lower portion of cap 6 and a snapping device 18 attached to cap 6 adjacent to slot 26 for use in selectively closing slot 26 as needed. During use of impotence aid invention 2, snapping device 18 is closed over slot 26. A bracket 14 is also centrally located on the bottom portion of cap 6 to facilitate the attachment of devices creating reciprocating movement (not shown), such as electric drills having a crank, jig saws, or electric knives, to provide massaging movement of cylinder 4 to cause additional enlargement of the penis (not shown) inserted into cylinder 4 until it is fully erect. A hole 12 positioned through bracket 14 is used for attachment of the reciprocating devices (not shown). Although hole 12 is shown to be round, and bracket 14 is shown to be tapered, the configurations of hole 12 and bracket 14 are not critical to impotence aid invention 2.

FIG. 2 shows collar 22 fired over the flared upper end of cylinder 4, the other end of cylinder 4 having external threads 16 for attachment to cap 6. FIG. 4 shows cap 6 having aperture 10 connecting through the side of cap 6 and being covered by one-way valve 8. In addition, FIG. 4 shows hole 12 positioned through bracket 14 on the bottom of cap 6 for connection to devices creating reciprocating movement (not shown). FIG. 3 shows both cap 6 and cylinder 4 attached to one another, with a condom 20 stretched between them. The use of condom 20 within cylinder 4 enhances stimulation of a penis (not shown) inserted therein to help maintain the penis in a fully erect condition. The open end of condom 20 is stretched over the flared upper end of cylinder 4 and held in place by collar 22, the lower end of condom 20 being connected through slot 26 in cap 6 by snapping device 18, which is contemplated to be a tight-fitting, stud-like device made of rubber material. Lubricant (not shown) may be applied to the inside of condom 20 and enhances stimulation to help enlarge the penis (not shown) inserted therein during massaging movement of cylinder 4. FIG. 3 also shows the same features of cap 6 shown in FIGS. 1 and 4, to include aperture 10 connecting through the side of cap 6 and covered by one-way valve 8, as well as hole 12 positioned through bracket 14 attached to the bottom of cap 6 for connection to devices creating reciprocating movement (not shown).

Similarly, FIGS. 5 and 6 show cap 6 having aperture 10 connecting through the side of cap 6 and covered by one-way valve 8, snapping device 18 attached to cap 6 adjacent to slot 26, and hole 12 positioned through bracket 14 attached to the bottom of cap 6 for connection to reciprocating devices (not shown). However, FIG. 5 is distinguished from FIG. 6 in that FIG. 5 shows snapping device 18 in an open position and FIG. 6 shows snapping device 18 in a closed position. In addition, FIGS. 6 and 7 show collar 22 having a central opening 24 therethrough, while FIG. 7 shows collar 22 positioned on the flared upper surface of cylinder 4.

Although the materials from which cylinder 4, cap 6, and one-way valve 8 are made is not critical to impotence aid invention 2, in the preferred embodiment it is contemplated for cylinder 4 and one-way cap 6 to be made of rigid plastic, and for one-way valve 8 to be made of rubber. It is also contemplated for valve 8 to be able to be disengaged for air to flow both in and out of cylinder 4. Also, the exact dimensions of the interior chamber formed by cylinder 4 and cap 6 are not critical to impotence aid invention 2 as long as it engages the outer surface of the penis (not shown) inserted therein when erect, in the preferred embodiment it is contemplated for the interior chamber formed by cylinder 4 and cap 6 to be approximately one and one-half inches in diameter and approximately seven inches long.

To use impotence aid invention 2, the interior of cylinder 4, or the inside surface of a condom inserted therein, would first be coated with a lubricant (not shown), such as a skin cream or petroleum jelly. Cap 6 would then be attached to cylinder 4 by mating threads 16 on cylinder 4 to cooperating threads (not shown) on internally threaded cap 6. Collar 22 would then be fitted over the flanged end of cylinder 4. It is contemplated for opening 24, centrally located through collar 22, to be of adequate size to allow insertion therethrough of a penis (not shown), but small enough to create a tight seal around the penis. As the penis is inserted completely within cylinder 4, displaced air (not shown) is forced out through one-way valve 8. When cylinder 4 is then partially drawn away from the penis, but not far enough to allow any additional air to enter into cylinder 4, a vacuum is created within cylinder 4 causing blood (not shown) to be drawn into the penis, thereby enlarging it. Although not shown, subsequent repeated movements of cylinder 4, by hand or through a device creating reciprocal movement, such as an electric drill with a crank, a jig saw, or an electric knife, will cause additional enlargement until the penis is fully erect. Continued reciprocal movement of cylinder 4 will most likely lead to ejaculation. Such devices creating reciprocal movement would be attached to hole 12 in bracket 14 which depends from cap 6. After full erection, one-way valve 8 may be disengaged. Condom 20 may be fitted into the interior of cylinder 4 to enhance stimulation of the penis (not shown). When used, the closed end of condom 20 would be inserted through slot 26 and secured to cap 6 by snapping device 18. The open end of condom 20 would be stretched over the flanged end of cylinder 4, lubricated, and secured into place by collar 22.

What is claimed is:

1. Apparatus for insertion therein of a penis for aiding in the drawing of blood into said penis thereby causing enlargement of said penis, said apparatus having a principle of operation similar to that of a conventional piston and cylinder assembly whereby said piston enters said conventional cylinder forcing air out of said conventional cylinder through a one-way air valve, said one-way air valve closing when said piston is drawn back thereby creating a vacuum within said conventional cylinder, said apparatus comprising an open-ended cylinder having a first open end with a plurality of external threads thereon and a second open end; an internally threaded cap having an aperture therethrough, said internal threading of said cap configured for mating with said external threads on said first open end, said cap attached to said first open end of said cylinder; a flexible collar having an opening therethrough, said opening of adequate size to allow insertion therethrough of said penis but small enough to create a tight seal around said penis, said flexible collar connected to said cylinder over said second open end; and a one-way valve positioned over said aperture in said cap so that when said penis is inserted into said cylinder said penis displaces air and said displaced air is forced out of said cylinder through said one-way valve and when said cylinder is partially drawn away from said penis, said one-way valve closes and a vacuum is created which causes said blood to be drawn into said penis forcing said enlargement thereof.

2. The apparatus of claim 1 wherein said second end of said cylinder is flanged.

3. The apparatus of claim 1 further comprising a bracket having a hole therethrough attached to said cap and a device capable of creating reciprocal movement, said device being attached to said hole for transferring said reciprocal movement to said cap and said cylinder for additional aid in maintaining said enlargement of said penis.

4. The apparatus of claim 1 further comprising a condom having a closed end and an open end, and wherein said cap also comprises a slot therethrough and a snapping device for plugging said slot, said closed end of said condom being inserted into said slot and held in place by said snapping device, and said open end of said condom being stretched across said second end of said cylinder between said cylinder and said collar so that when said penis is inserted into said condom, said condom further aids in maintaining said enlargement of said penis.

5. Apparatus for insertion therein of a penis for aiding in the drawing of blood into said penis thereby causing enlargement of said penis, said apparatus having a principle of operation similar to that of a conventional piston and cylinder assembly whereby said piston enters said conventional cylinder forcing air out of said conventional cylinder through a one-way air valve, said one-way air valve closing when said piston is drawn back thereby creating a vacuum within said conventional cylinder, said apparatus comprising an open-ended cylinder having a first open end with a plurality of external threads thereon and a second open end; an internally threaded cap having an aperture therethrough, said internal threading of said cap configured for mating with said external threads on said first open end, said cap attached to said first open end of said cylinder; a flexible collar having an opening therethrough, said opening of adequate size to allow insertion therethrough of said penis but small enough to create a tight seal around said penis, said flexible collar connected to said cylinder over said second open end; and a one-way valve positioned over said aperture in said cap so that when said penis is inserted into said cylinder said penis displaces air and said displaced air is forced out of said cylinder through said one-way valve and when said cylinder is partially drawn away from said penis, said one-way valve closes and a vacuum is created which causes said blood to be drawn into said penis forcing said enlargement thereof, said apparatus further comprising a bracket having a hole therethrough attached to said cap and a device capable of creating reciprocal movement, said device being attached to said hole for transferring said reciprocal movement to said cap and said cylinder for additional aid in maintaining said enlargement of said penis.

6. The apparatus of claim 5 wherein said second end of said cylinder is flanged.

7. The apparatus of claim 5 further comprising a condom having a closed end and an open end, and wherein said cap also comprises a slot therethrough and a snapping device for plugging said slot, said closed end of said condom being inserted into said slot and held in place by said snapping device, and said open end of said condom being stretched across said second end of said cylinder between said cylinder and said collar so as to further aid in maintaining said enlargement of said penis.

8. A method for aiding and maintaining the enlargement of a penis, said method comprising the steps of providing a penis, a quantity of lubricant, a cylinder having a first open end with a plurality of external threads thereon, a second open end and an interior, an internally threaded cap having an aperture therethrough, said internal threading of said cap configured for mating with said external threads on said first open end, a one-way valve positioned over said aperture so as to close said aperture, and a flexible collar having an opening therethrough, said opening of adequate size to allow insertion therethrough of said penis but small enough to create a tight seal around said penis; coating said interior of cylinder with said lubricant; attaching said cap to said cylinder by mating said external threads on said cylinder to said internally threaded cap; positioning said one-way valve over said aperture to allow air to only flow from said cylinder; fitting said collar over said second of said cylinder; inserting said penis completely within said cylinder to displace said air from said cylinder and force said air out of said cylinder through said one-way valve; and partially drawing cylinder away from said penis to create a vacuum within said cylinder for causing said enlargement of said penis.

9. The method of claim 8 wherein said second end of said cylinder is flanged.

10. The method of claim 8 further comprising the steps of providing a bracket having a hole therethrough depending from said cap and a device capable of creating reciprocal movement; attaching said device to said hole; activating said device to transfer said reciprocal movement to said cap and said cylinder for additional aid in maintaining said enlargement of said penis.

11. The method of claim 8 wherein said cap also comprises a slot therethrough and a snapping device for plugging said slot, and further comprising the steps of providing a condom having a closed end, an open end, and an inside surface; inserting said closed end of said condom into said slot; securing said closed end in place with said snapping device; stretching said open end of said condom across said second end of said cylinder; lubricating said inside surface with said lubricant; and securing said condom across said second end so as to further aid in maintaining said enlargement of said penis.

* * * * *